United States Patent [19]

Muto et al.

[11] Patent Number: 6,048,956
[45] Date of Patent: Apr. 11, 2000

[54] DIGLYCIDYL ETHERS

[75] Inventors: Kenji Muto; Toshikazu Murayama; Nobuko Tsuzaki, all of Yokkaichi, Japan

[73] Assignee: Kyowa Yuka Co., Ltd., Tokyo, Japan

[21] Appl. No.: 09/180,148

[22] PCT Filed: Mar. 3, 1998

[86] PCT No.: PCT/JP98/00861

§ 371 Date: Nov. 3, 1998

§ 102(e) Date: Nov. 3, 1998

[87] PCT Pub. No.: WO98/39314

PCT Pub. Date: Sep. 11, 1998

[30] Foreign Application Priority Data

Mar. 4, 1997 [JP] Japan ..................................... 9-048632

[51] Int. Cl.[7] ............................. C08G 59/68; C08G 65/10
[52] U.S. Cl. .......................... 528/93; 523/456; 528/103; 528/103.7; 549/555
[58] Field of Search .............................. 523/456; 528/93, 528/103, 103.7; 549/555

[56] References Cited

U.S. PATENT DOCUMENTS 4,417,033   11/1983   Bowditch .

FOREIGN PATENT DOCUMENTS

| 2 527 606 | 4/1983 | France . |
| 58-219173 | 12/1983 | Japan . |
| 2 122 609 | 1/1984 | United Kingdom . |

*Primary Examiner*—Robert Dawson
*Assistant Examiner*—D. Aylward
*Attorney, Agent, or Firm*—Finnegan, Henderson, Farabow, Garrett & Dunner, L.L.P.

[57] ABSTRACT

The present invention relates to a diglycidyl ether represented by the following general formula (I):

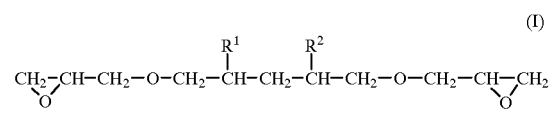

(wherein, $R^1$ and $R^2$ are the same or different, and represent lower alkyl having 1~6 carbon atoms), a composition including the glycidyl ether and epoxy resin, and epoxy resin cured product obtained by the composition. The glycidyl ether can be used as a reactive diluent for epoxy resins.

7 Claims, No Drawings

DIGLYCIDYL ETHERS

TECHNICAL FIELD

The present invention relates to a glycidyl ether useful as a reactive diluent for epoxy resins, a composition containing the glycidyl ether, and epoxy resin cured product.

BACKGROUND ART

Epoxy resins demonstrate good adhesion to a variety of materials to be coated, limited contraction upon curing, excellent resistance to heat, chemicals, and solvents, and excellent electrical insulatingproperties and the like. Accordingly, epoxy resins are widely used as coating materials, printing ink, and adhesives.

However, epoxy resins are brittle, and cracks occur due to thermal shock or stress-strain when cured or used.

In order to resolve these problems and to facilitate handling of the epoxy resin, a technique is known in which a diluent is employed in the epoxy resin.

Polyglycidyl ethers of aliphatic polyoyls are known for use as epoxy resin diluents. In general, they have low viscosity, with two or more epoxy groups in the molecule. Specific examples of such polyglycidyl ethers of aliphatic polyols include polyglycidyl ethers of 1,6-hexanediol, neopentylglycol, and trimethylolpropane and the like. In addition, U.S. Pat. No. 4,481,348 discloses *glycidyl ethers derived from 2-butyl-2-ethyl-1,3-propanediol. However, such glycidyl ethers do not impart sufficient flexibility to the epoxy resin, and thus are not satisfactory in terms of their practical applications.

DISCLOSURE OF THE INVENTION

The present invention provides a diglycidyl ether represented by the following general formula (I):

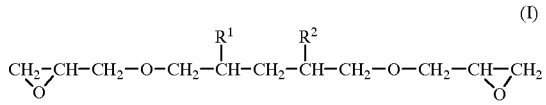

(wherein, $R^1$ and $R^2$ are the same or different, and represent lower alkyl having 1~6 carbon atoms), and provides a reactive diluent for an epoxy resin containing a diglycidyl ether represented by the above general formula (I).

The present invention also provides a composition containing an epoxy resin and the diglycidyl ether represented by the above general formula (I), and an epoxy resin cured product obtained by adding a curing agent to the composition and curing the composition.

In addition, the present invention also provides a method for curing an epoxy resin in which the aforementioned diglycidyl ether is mixed with an epoxy resin, a curing agent is added to the mixture, and the mixture is cured.

MODES FOR CARRYING OUT THE INVENTION

In the definition for the general formula (I) in the present invention, $R^1$ and $R^2$ are lower alkyl having 1~6 carbon atoms and are either a linear or branched chain. Examples include methyl, ethyl, propyl, isopropyl, butyl, isobutyl, tert-butyl, pentyl, isopentyl, neopentyl, hexyl and the like.

Diglycidyl ether of the present invention represented by general formula (I) can be obtained by reacting epihalohydrin and 2,4-dialkyl-1,5-pentanediol having $R^1$ and $R^2$ at positions 2 and 4 in a two-phase system of an organic solvent phase and a solid phase in the presence of a solid alkali and a phase transfer catalyst [see Synthesis, p. 649 (1985), for example].

Specific examples of 2,4-dialkyl-1,5-pentanediol which is one of the starting materials the diglycidyl ether of the present invention represented by general formula (I) include 2,4-dimethyl-1,5-pentanediol, 2-ethyl-4-methyl-1,5-pentanediol, 2-methyl-4-propyl-1,5-pentanediol, 2-isopropyl-4-methyl-1,5-pentanediol, 2,4-diethyl-1,5-pentanediol, 2-ethyl-4-propyl-1,5-pentanediol, 2-ethyl-4-isopropyl-1,5-pentanediol, 2,4-dipropyl-1,5-pentanediol, 2-isopropyl-4-propyl-1,5-pentanediol, 2,4-diisopropyl-1,5-pentanediol, 2,4-dibutyl-1,5-pentanediol, 2,4-dipentyl-1,5-pentanediol, 2,4-dihexyl-1,5-pentanediol and the like.

These 2,4-dialkyl-1,5-pentanediols can be produced using a known method. Preferably, 2,4-dialkyl-1,5-pentanediols are produced by reacting formaldehyde with 2-butenal derivative represented by general formula (III) (step 1), and then hydrogenating a mixture of the thus obtained reaction products (IV) and (V) (step 2) as disclosed in Japanese Published Unexamined Patent Application No. 48642/96 or in EP807617A.

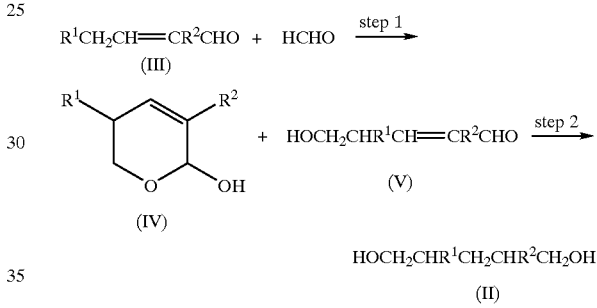

A 2-butenal derivative represented by general formula (III) is obtained by aldol condensation of one or two types of aldehydes and dehydration reaction.

In step 1, reaction between formaldehyde and a 2-butenal derivative represented by general formula (III) is carried out using a basic catalyst preferably in the presence of a water soluble organic solvent at 15~100° C., preferably at 30~80° C. The molar ratio of formaldehyde based on the butenal derivative is in the range of 0.4~2, and preferably in the range of 0.5~1.5.

Examples of the basic catalyst employed in step 1 include such alkaline metal hydroxides such as lithium hydroxide, sodium hydroxide, and potassium hydroxide; alkaline earth metal hydroxides such as calcium hydroxide and magnesium hydroxide; alkali metal carbonates such as sodium carbonate and potassium carbonate; sodium alcoholates such as sodium methylate, sodium ethylate, and sodium butylate; tertiary amines such as triethylamine and tributylamine; quaternary ammonium hydroxides such as benzyltrimethylammonium hydroxide and tetrabutylammonium hydroxide; and strong basic ion-exchange resins. The catalyst is employed in an amount such that its molar ratio based on the 2,4-diethyl-1,5-pentanediol is 0.01~0.5, and preferably 0.02~0.3.

The water soluble organic solvent employed in step 1 is not particularly limited, provided that it is inert under the reaction conditions. For example, alcohols such as methanol, ethanol, propanol, isopropyl alcohol, ethylene glycol, and propylene glycol; ethers such as dimethoxyethane, tetrahydrofuran, and dioxane; and glycol ethers such as ethylene glycol monoethyl ether may be suitably employed. The amount of the water soluble organic solvent employed is not particularly limited, but is preferably 100% by weight or less of the total amount of the 2-butenal derivative and formalin employed.

Impurities are removed from the mixture of compound (IV) and compound (V) obtained in step 1, preferably by a usual method such as neutralizing, concentrating, separating or washing with water. A mixture of compound (IV) and compound (V) obtained in step 1 is then subjected to hydrogenation reaction by dispersing or suspending a hydrogenation catalyst in a suitable solvent or without solvent, in the presence of hydrogen, or by supplying a solution of the mixture of compound (IV) and compound (V) obtained in step 1 to a reaction tube filled with the hydrogenation catalyst. The hydrogenation reaction is carried out at 30~200° C., and preferably 50~150° C., at a hydrogen pressure of 1~150 kg/cm$^2$, and preferably 5~80 kg/cm$^2$ (step 2).

The solvent employed in step 2 is not particularly limited provided that it is inert under the reaction conditions. Suitable examples thereof include various alcohols such as methanol, ethanol, propanol, isopropyl alcohol, and butanol; ethers such as dimethoxyethane, tetrahydrofuran, and dioxane; water; or mixed solvents thereof. Examples of hydrogenation catalysts include those containing one or more of metals such as nickel, ruthenium, platinum, copper, or rhodium, as the catalytic active component. They may further include metals such as chrome, zinc, barium, aluminum, magnesium, tungsten or the like. After completion of the reaction, the target 2,4-dialkyl-1,5-pentanediol can be obtained from the reaction mixture by a usual method, for example, distilling off low boiling point compounds from the reaction mixture at normal or reduced pressure after the catalyst has been removed, and then purifying the obtained residue by distillation under reduced pressure.

Specific examples of the epihalohydrin which is reacted with 2,4-dialkyl-1,5-pentanediol in order to obtain the diglycidyl ether of the present invention include epichlorohydrin, epibromohydrin, epuiodohydrin and the like. The amount of epihalohydrin employed is about 1~12 moles, and preferably 2~8 moles, based on 1 mole of 2,4-dialkyl-1,5-pentanediol.

Examples of the solid alkali employed in the reaction between 2,4-dialkyl-1,5-pentane diol and epihalohydrin include hydroxides or carbonates of alkali metals or hydroxides or carbonates of alkaline earth metals, for example, sodium hydroxide, potassium hydroxide, sodium carbonate, potassium carbonate, and the like. The amount of the solid alkali employed is not particularly limited, but is preferably in the range of 1~5 moles based on 1 mole of 2,4-dialkyl-1,5-pentanediol. Solid alkali may be used alone, or in mixtures of two or more. Solid alkali may be used together with water. The amount of water is generally the same weight or less than that of the solid alkali.

Examples of the phase transfer catalyst employed in the reaction between 2,4-dialkyl-1,5-pentanediol and epthalohydrin include quaternary ammonium salts and quaternary phosphonium salts, such as tetraethylammonium chloride, tetrabutylammonium bromide, tetrabutylammonium sulfate, ethyltriphenylphosphonium bromide, and the like. The phase transfer catalyst is employed in an amount of 0.5~5 mole % based on the epihalohydrin.

In general, the reaction between 2,4-dialkyl-1,5-pentanediol and epihalohydrin is carried out at about 20~90° C., and preferably, at 30~60° C. If the reaction temperature is too low, the rate of the primary reaction is slowed. Conversely, if the reaction temperature is too high, side reactions generating high polymer compounds or the like are promoted.

A reaction solvent may be employed, if necessary, in the reaction between 2,4-dialkyl-1,5-pentanediol and epihalohydrin, examples thereof including such aliphatic and alicyclic hydrocarbons such as hexane, octane, and cyclohexane; aromatic hydrocarbons such as benzene and toluene; aliphatic halides such as dichloromethane and chloroform; and aliphatic and alicyclic ethers such as diethyl ether and tetrahydrofuran.

This reaction is carried out by a two-phase system of an organic solvent phase and a solid phase. In the reaction, it is desirable to stir the mixture so that there is satisfactory contact between the reactants.

After completion of the reaction, precipitates are removed by filtration, and purification is performed by a usual method such as washing with water, distilling, etc., to obtain the desired compound.

In place of the method described above, synthesis of the diglycidyl ether of the present invention may also be accomplished by means of a two-step reactions method in which a halohydrin ether is synthesized from 2,4-dialkyl-1,5-pentanediol and epihalohydrin using an acidic catalyst such as sulfuric acid, boron trifluoride or tin tetrachloride, and the halohydrin ether is then ring-opened by reacting with alkali; or by means of a method in which 2,4-dialkyl-1,5-pentanediol and epihalohydrin are reacted in an alkaline aqueous solution. In these case, however, side reactions via the epoxy groups tend to occur, which results in reduction of the yield of the desired product.

Specific examples of the diglycidyl ether of the present invention represented by general formula (I) obtained in aforementioned way include 2,4-dimethyl-1,5-pentanediol diglycidyl ether, 2-ethyl-4-methyl-1,5-pentanediol diglycidyl ether, 2,4-diethyl-1,5-pentanediol diglycidyl ether, 2-ethyl-4-propyl-1,5-pentanediol diglycidyl ether, 2,4-dipropyl-1,5-pentanediol diglycidyl ether, 2-isopropyl-4-methyl-1,5-pentanediol diglycidyl ether, 2-ethyl-4-isopropyl-1,5-pentanediol diglycidyl ether, 2,4-diisopropyl-1,5-pentanediol diglycidyl ether, 2-isopropyl-4-propyl-1,5-pentanediol diglycidyl ether, and the like. Among them, 2,4-diethyl-1,5-pentanediol diglycidyl ether is preferred.

The diglycidyl ether of the present invention has a low viscosity and imparts flexibility and toughness, and therefore, it can be preferably employed as a reactive diluent for epoxy resins.

As the aforementioned epoxy resin, known epoxy resins may be employed, including bisphenol A epoxy resin, phenol novolak epoxy resin, cresol novolak epoxy resin, brominated bisphenol A epoxy resin, bisphenol F novolak epoxy resin, brominated phenol novolak epoxy resin, and naphthol novolak epoxy resin. However, the aforementioned epoxy resin is not limited to the above epoxy resins.

The amount of the glycidyl ether of the present invention used as a reactive diluent for the aforementioned epoxy resin is not particularly limited, but is preferably in the range of 10~50% by weight based on the epoxy resin.

When being employed as the reactive diluent for epoxy resins, the diglycidyl ether of the present invention may be used alone or in combination with other polyfunctional diglycidyl ethers, such as trimethylolpropane triglycidyl ether, 1,6-hexane diol diglycidyl ether, neopentylglycol diglycidyl ether, and the like.

By adding a curing agent to a composition comprising the diglycidyl ether of the present invention and an epoxy resin, and curing using a conventional epoxy resin curing method, an epoxy resin cured product having a structure incorporating the aforementioned diglycidyl ether component can be obtained.

Known epoxy resin curing agents may be employed as the curing agent cited here, examples including amines such as ethylenediamine, diethylenetriamine, triethylenetetramine, dimethylaminopropylamine, diethylaminopropylamine, piperidine, pyridine, metaphenylenediamine, methylenedianiline, diaminodiphenylsulfone, and 1-cyanoguanadine; organic acids (anhydrides) such as oxalic acid, phthalic anhydride, maleic anhydride, hexahydrophthalic anhydride, pyromellitic dianhydride, and dichloromaleic anhydride; and latent curing agents such as dicyandiamide, imidazole, $BF_3$-amine complex, and guanidine derivatives. Among them, amines are preferably employed. Among amines, triethylenetetramine is more preferable.

The amount of curing agent employed is not particularly limited, provided that it is an amount sufficient to cure the epoxy resin. When employing an amine for the curing agent, it is preferable that the amine is added so that the amine mole number calculated from the amine equivalent weight (amine molecular weight/active hydrogen atom number) for the amine employed as the curing agent is equal to the mole number of total epoxy groups in the composition comprising the aforementioned epoxy resin and the diglycidyl ether. Similarly, when an acid anhydride is employed as the curing agent, it is preferable that the acid anhydride is added so that the mole number of acid anhydride groups employed as the curing agent is equal to the mole number of total epoxy groups in the composition comprising the epoxy resin and the diglycidyl ether.

Since the duration and temperature of curing for the composition comprising the aforementioned epoxy resin and the diglycidyl ether will vary depending on types of the epoxy resin, a curing agent and material to be coated that are employed, these values are not specifically limited. Generally, curing is carried out at from room temperature to 200° C.

Known curing accelerator may be suitably employed, such as tertiary amines, imidazole, organic acid metallic salts, Lewis acids, amine complex salts, phosphorous compounds, or a mixture thereof.

The flexibility and toughness of the epoxy resin cured product thus obtained is superior to epoxy resin cured products containing known diluents.

The various known additives may be added to the epoxy resin cured product of the present invention, if necessary, these additives including fillers like crystallizable silica powder, melted silica powder, alumina powder, talc, quartz glass powder, calcium carbonate powder, or fiberglass; coloring agents; flame retardants; mold releasing agents; and coupling agents.

Examples will now be employed to explain the present invention. The present invention is not limited to the following, however.

EXAMPLE 1

32 g of 2,4-diethyl-1,5-pentanediol, 74 g of epichlorohydrin, 32 g of sodium hydroxide, 3.2 g of distilled water, and 0.9 g of tetrabutylammonium bromide were placed in a 300 ml reaction vessel equipped with a stirrer, thermometer, ref lux condensing tube, and gas introduction tube, and heated at 45~50° C. under a nitrogen gas flow to carry out the reaction. The progress of the reaction was confirmed by gas chromatography under the analysis conditions noted below. The reaction is continued until the starting materials and mono-substituted glycidyl ether were almost entirely exhausted.

After the reaction, the organic layer was separated by filtration, and washed with water twice. The obtained product was then purified under reduced pressure distillation. The purified product had a boiling point of 126~129° C./0.3 torr, and an isolated yield of 60% (based on a starting diol). The epoxy equivalent weight measured according to the ISO 3001 method (tetraethylammonium bromide-perchloric acid method) was 142. In the comparative examples shown below, the epoxy equivalent weight was measured using the same method.

Next, the obtained product was analyzed using $^1$H-NMR, $^{13}$C-NMR, IR spectral analysis.

The main absorption wavelength in the IR spectrum was as follows.

IR (NaCl; cm$^{-1}$) 2960, 2927, 2875, 1464, 1381, 1336, 1254, 1159, 1103, 912, 849.

The results of analysis of the obtained product using $^1$H-NMR and $^{13}$C-NMR are as follows.

$^1$H-NMR (CDCl$_3$: ppm); 0.88 (6H, t, J=7.6 Hz), 1.17~1.44 (6H,m), 1.57~1.64 (2H,m), 2.59~2.61 (2H,m), 2.77~2.79 (2H,m), 3.12~3.14 (2H,m), 3.35~3.40 (6H,m), 3.67~3.71 (2H,m); $^{13}$C-NMR (CDCl$_3$: ppm); 74.6, 71.6, 50.9, 44.2, 37.4, 32.7, 24.3, 10.9

(Conditions for gas chromatography analysis)
column filling agent: SE-30 (manufactured by GL Science Inc.)
column size: length 1.6 m, inner diameter 3.2 mm
detector: FID
injection temperature: 290° C.
detector temperature: 290° C.
column temperature: rising from 100° C. to 290° C. (10° C./min)
air flow volume: 50 kP
H$_2$ flow volume: 60 kP
N$_2$ flow volume: 40 ml/min

COMPARATIVE EXAMPLE 1

1,5-Pentanediol diglycidyl ether was obtained by conducting the reaction substantially in the same manner as Example 1 except that 20.8 g of 1,5-pentanediol was employed instead of 2,4-diethyl-1,5-pentanediol. The epoxy equivalent weight of the obtained product was 111.

COMPARATIVE EXAMPLE 2

3-Methyl-1,5-pentanediol diglycidyl ether was obtained by conducting the reaction substantially in the same manner as Example 1 except that 23.6 g of 3-methyl-1,5-pentanediol was employed instead of 2,4-diethyl-1,5-pentanediol. The epoxy equivalent weight of the obtained product was 118.

COMPARATIVE EXAMPLE 3

2-Butyl-2-ethyl-1,3-propanediol diglycidyl ether was obtained by conducting the reaction substantially in the same manner as Example 1 except that 32 g of 2-butyl-2-ethyl-1,3 propanediol was employed instead of the 2,4-diethyl-1,5-pentanediol. The epoxy equivalent weight of the obtained product was 152.

Next, mixed solutions were prepared containing as the epoxy resin 75 parts by weight of bisphenol A diglycidyl ether (product name: Epicoat 828, manufactured by Yuka Shell Epoxy Co. Ltd.), and as the diluent 25 parts by weight of diglycidyl ether obtained in Example 1, Comparative Examples 1–3 or a commercially available product. The viscosity (25° C.) of the mixtures was measured. Table 1 shows the viscosity (25° C.) of the diglycidyl ethers obtained in Example 1, Comparative Examples 1–3, or a commercially available product and the mixtures when the above diglycidyl ethers were blended with Epicoat 828.

TABLE 1

Viscosity of various diglycidyl ethers

| | Monomer | viscosity (25° C.) units: cps | viscosity when blended with Epicoat 828 (25° C.) units: ps |
|---|---|---|---|
| Example 1 | 2,4-diethyl-1,5-pentanediol diglycidyl ether | 13 | 6.6 |
| Comp. Ex. 1 | 1,5-pentanediol diglycidyl ether | 9 | 3.5 |
| Comp. Ex. 2 | 3-methyl-1,5-pentanediol diglycidyl ether | 10 | 4.4 |
| Comp. Ex. 3 | 2-butyl-2-ethyl-1,3-propanediol diglycidyl ether | 20 | 8.6 |
| Commercially available product | 1,6-hexanediol diglycidyl ether 1) | 18 | 5.8 |
| Commercially available product | Neopentyl glycol diglycidyl ether 2) | 17 | 8.4 |
| Commercially available product | Trimethyolpropane triglycidyl ether 3) | 28 | 21.4 |

Viscosity of Epicoat 828 alone: 137 ps (25° C.)

1) Epolite 1600 manufactured by Kyoeisha Chemical Co.,LTD

2) Epolite 1500NP manufactured by Kyoeisha Chemical Co.,LTD

3) Epolite 100 MF manufactured by Kyoeisha Chemical Co.,LTD

EXAMPLE 2, COMPARATIVE EXAMPLES 4–8

12.5 g of the diglycidyl ether synthesized in Example 1 or Comparative Examples 1–3, or a commercially avaiable diglycidyl ether, 37.5 g of bisphenol A diglycidyl ether (product name: Epicoat 828, manufactured by Yuka Shell Epoxy Co. Ltd.) as an epoxy resin, and triethylenetetramine as a curing agent, were added so that the amine mole number calculated from the amine equivalent weight equaled the mole number of total epoxy groups in the composition. The mixture was held at room temperature for 24 hours, and then at 115° C. for 2 hours, to obtain a cured film. Tensile tests were then carried out on the cured film according to the method described under JIS K7113. The results are shown in Tables 2 and 3.

The fracture energy relative value was defined to be 100 when no blend was employed (Epicoat 828 only), and was calculated from the area surrounded by the stress-strain curve in the tensile test.

TABLE 2

Mechanical properties of cured film

| | Blended diglycidyl ether | Strength Kg/cm$^2$ *1) | elongation % | Young's modulus kg/mm$^2$ |
|---|---|---|---|---|
| Example 2 | 2,4-diethyl-1,5-pentanediol diglycidyl ether | 555 560 | 13 | 158 |
| Comp. Ex. 4 | 1,5-pentanediol diglycidyl ether | 484 502 | 10 | 168 |
| Comp. Ex. 5 | 3-methyl-1,5-pentanediol diglycidyl ether | 490 511 | 11 | 175 |
| Comp. Ex. 6 | 2-butyl-2-ethyl-1,3-propanediol diglycidyl ether | 547 577 | 8 | 173 |
| Comp. Ex. 7 | 1,6-hexanediol diglycidyl ether 1) | 523 591 | 7 | 164 |
| Comp. Ex. 8 | No blend | 683 | 8 | 202 |

*1) strength
upper row: breaking strength
lower row: yielding point strength

TABLE 3

Mechanical properties of cured film

| | blended diglycidyl ether | Breaking strength (relative value) |
|---|---|---|
| Example 2 | 2,4-diethyl-1,5-pentanediol diglycidyl ether | 110 |
| Comp. Ex. 4 | 1,5-pentanediol diglycidyl ether | 91 |
| Comp. Ex. 5 | 3-methyl-1,5-pentanediol diglycidyl ether | 97 |
| Comp. Ex. 6 | 2-butyl-2-ethyl-1,3-propanediol diglycidyl ether | 70 |
| Comp. Ex. 7 | 1,6-hexanediol diglycidyl ether | 66 |
| Comp. Ex. 8 | no blend | 100 |

The results in Table 2 show that a cured film in which the 2,4-diethyl-1,5-pentanediol diglycidyl ether of the present invention has been blended demonstrates considerable elongation and little reduction in tensile strength. Young's modulus values obtained in tensile tests are a measure of how readily deformation occurs. The diglycidyl ether of the present invention had a Young's modulus value which was extremely small compared to the other examples, indicating substantial flexibility.

From the results in Table 3, it is clear that the fracture energy of a cured film in which the diglycidyl ether of the present invention has been blended is larger than those of the other examples, indicating superior toughness.

The results in Tables 2 and 3 demonstrate that the 2,4-diethyl-1,5-pentanediol diglycidyl ether of the present invention is a reactive diluent for epoxy resins which provides the most flexibility and toughness as compared to the diglycidyl ethers of the comparative examples.

INDUSTRIAL APPLICABILITY

The glycidyl ether of the present invention is useful as a reactive diluent for epoxy resins. Epoxy resin cured products containing the diglycidyl ether may be widely used, for example, applications as adhesive agents, coating materials, laminates, molding materials, injection materials and the like. However, due to its superior flexibility and toughness, the glycidyl ether of the present invention is particularly useful as adhesive agents and coating materials.

We claim:

1. A diglycidyl ether represented by the following general formula (I):

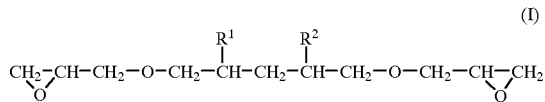

(I)

(wherein, $R^1$ and $R^2$ are the same or different, and represent lower alkyl having 1~6 carbon atoms).

2. The diglycidyl ether according to claim 1, wherein $R^1$ and $R^2$ in general formula (I) are ethyl groups.

3. A reactive diluent for epoxy resins comprising the diglycidyl ether according to claim 1 or claim 2.

4. A composition containing an epoxy resin and the diglycidyl ether according to claim 1 or claim 2.

5. The composition according to claim 4 comprising a curing agent.

6. An epoxy resin cured product obtained by curing the composition according to claim 5.

7. A method for curing an epoxy resin wherein the diglycidyl ether according to claim 1 or claim 2 is mixed with an epoxy resin, a curing agent is added to the mixture, and the mixture is cured.

* * * * *